United States Patent
Lo et al.

(10) Patent No.: US 8,263,388 B2
(45) Date of Patent: Sep. 11, 2012

(54) METHOD AND APPARATUS FOR DETECTING SPECIFIC DNA SEQUENCES

(75) Inventors: Chun Lap Samuel Lo, Hong Kong (HK); Derek Siu Wing Or, Hong Kong (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 230 days.

(21) Appl. No.: 12/813,488

(22) Filed: Jun. 10, 2010

(65) Prior Publication Data

US 2011/0306050 A1    Dec. 15, 2011

(51) Int. Cl.
C12M 1/00 (2006.01)
C12Q 1/68 (2006.01)
C12Q 1/56 (2006.01)

(52) U.S. Cl. .................. 435/283.1; 435/6.11; 435/13

(58) Field of Classification Search .................. None
See application file for complete search history.

(56) References Cited

U.S. PATENT DOCUMENTS

| | | | |
|---|---|---|---|
| 6,875,619 | B2 | 4/2005 | Blackburn |
| 2003/0190608 | A1 | 10/2003 | Blackburn |
| 2005/0227275 | A1 | 10/2005 | Jung et al. |
| 2010/0279885 | A1 * | 11/2010 | Gu et al. .......................... 506/9 |

* cited by examiner

*Primary Examiner* — Samuel Woolwine
*Assistant Examiner* — Suchira Pande
(74) *Attorney, Agent, or Firm* — The Hong Kong Polytechnic University

(57) ABSTRACT

An apparatus for detecting the presence of a microorganism in a sample includes a housing that includes a base fixed with a first DNA primer having a nucleotide sequence that is complementary to a DNA sequence of the microorganism of interest, a fibrinogen-splitting agent that is bound with a second DNA primer having a nucleotide sequence that is also complementary to a DNA sequence of the microorganism of interest, a rinsing unit configured to rinse the housing; and a fibrinogen adding unit configured to add fibrinogen to the housing so that the fibrinogen chemically reacts with the fibrinogen-splitting agent to produce a viscous substance, an ultrasonic emitter configured to emit ultrasonic signal to the housing, and an ultrasonic receiver configured to receive ultrasonic signal from the housing and transmit the received ultrasonic signal to an ultrasonic analyzer, wherein the ultrasonic analyzer determines whether the microorganism of interest exists.

10 Claims, 5 Drawing Sheets

METHOD AND APPARATUS FOR DETECTING SPECIFIC DNA SEQUENCES

BACKGROUND OF THE INVENTION

1. Field of the Invention

Figure 1:
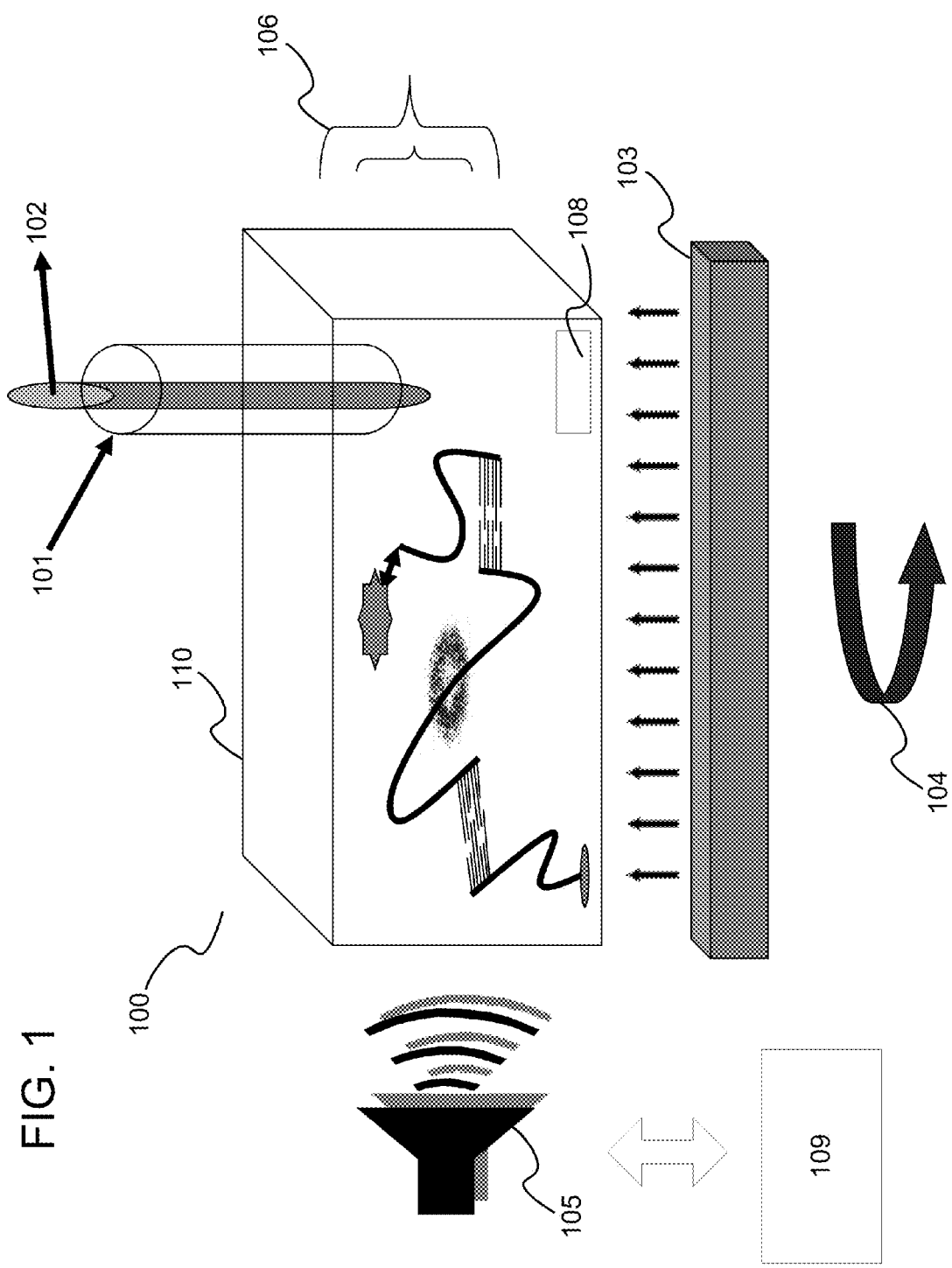

The present invention relates to detecting the presence of a microorganism in a sample by detecting the presence of its specific DNA sequence using a combination of complementary DNA sequences with one linked to a fibrinogen-splitting enzyme-based bio-chemo-physical conversion method and an ultrasonic microorganism detection apparatus.

2. Description of the Related Art

A variety of methods exists in the detection of the presence of a biological analyte, for examples, enzyme immunoassay (EIA), radioimmunoassay (RIA), enzyme-linked immunosorbent assay (ELISA), polymerase chain reaction (PCR), real-time-PCR (RT-PCR), etc. These methods have been used to measure levels of hormones, antigens, antibodies, enzymes, proteins, drugs, specific stretches, etc. of DNAs and pollutants.

Among these methods, the most popular ones are PCR and RT-PCR in which samples containing microorganisms of interest will have their DNAs extracted. Then, the genomic double strand DNAs will be heated to 94-96° C. and held for 1-9 minutes so that the hydrogen bonds between the complementary bases of the DNA strands break and give single strands of DNA. In order to detect the presence of a microorganism of interest in a sample, complementary DNA oligonucleotide primers (e.g. F#1 and R#1 for forward and reverse sequences, respectively) are added to bind to adjacent stretches of DNA sequences that are either up-stream or down-stream of this specific stretch of DNA (in the single strands of DNA) of interest (sequence #1). Stable DNA-DNA hydrogen bonds will be formed when the primer sequences match very closely the template sequence, and the process is referred to as annealing. The reaction temperature will then be lowered to 50-65° C. before being kept for 20-40 seconds. With the addition of deoxynucleotide triphosphates and through the actions of DNA polymerase (e.g. Taq polymerase), a DNA fragment (called sequence #2) which is complementary to this specific sketch of DNA of interest (sequence #1) and indicative of the presence of microbes of interest will be manufactured. Sequence #1 is said to be transcribed and sequence #2 is formed. This is called the extension/elongation step. With repeated cycles of warming up (90° C.) and cooling down (50 to 65° C.), sequence #1 will be transcribed many times (usually 30-35 times) before the final elongation step (70 to 74° C. for 15 minutes). This ensures that any remaining single-stranded DNA is fully extended. With the PCR method, the mixture containing the transcribed stretches of specific DNA (i.e. sequence #2, the primers, the enzymes, etc.) will have to be resolved with agarose gel electrophoresis using 1% agarose gels. These DNA fragments and primers will be resolved by their molecular weights. Visualization of the DNA fragments is achieved by the addition of ethidium bromide under ultra-violet (UV) lights. If the microorganism of interest is present in the sample, after the PCR steps, an UV-absorbing DNA band of the right molecular size as the complementary DNA (sequence #2) will be present. Subsequently, this PCR product (supposedly sequence #2) has to be inserted in a bacteriophage vector system (e.g. pGEM-T) before being expressed in a host bacterium (e.g. *E. Coli*). DNA sequence of this DNA band (i.e. sequence #2) can then be investigated using traditional dideoxy methods. If and when sequencing results obtained for this PCR product (experimentally obtained sequence #2) is complementary to that of sequence #1, the test will be considered affirmative. On the other hand, with the RT-PCR method, DNA binding dyes (such as Cyanine green dyes) will be added to the reaction mixture (with all the other reagents) in the initial heating step. With similar experimental conditions to those of the PCR method, if the specific sketch of DNA (sequence #1) is present in the sample, it will be transcribed by the DNA polymerase presented. Many copies of sequence #2 will be produced with repeatedly transcribed. As the amount of DNA sequences increases and with the presence of DNA binding dyes, the amount of dyes bound to the DNA will be increased. This dye has the unique fluorescent characteristics and will fluoresce when bound to DNA. Therefore, an increased florescence not only indicates the presence of this complementary DNA sequence (sequence #2) that is indicative of the presence of this microorganism sequence of interest (sequence #1) and hence the microorganism of interest, but also indicates the number of copies of this sketch of DNA (sequence #1) in the microorganism of interest.

Nonetheless, these PCR and RT-PCR methods, while capable of being used on-site for field operations, they involve relatively heavy instrumentation as they rely on fluorescence to detect and quantify levels of the analyte presented. Hence, these methods with relatively heavy instrumentation are not suitable for on-site field operations.

The present invention does not require a florescence source to detect the presence of a microorganism of interest. In addition, each component shown in FIG. 1 can be only a few centimeters large. As such, the size of the microorganism detection apparatus can be relatively small (e.g. 18 cm long, 8 cm wide and 5 cm tall as in our prototype). Furthermore, the microorganism detection apparatus can be wholly battery operated. Thus, the apparatus can be operated at a remote location without regular electrical power supply. Due to its light-weight, portability and the simplicity of operation, the apparatus is suitable for handheld on-site field operations. Through the present invention, the disadvantages of prior detection methods and apparatuses are overcome and benefits are realized in the field of biological analyte analysis.

SUMMARY OF THE INVENTION

According to an aspect of the present invention, the present invention provides a method embedded within an apparatus for detecting the presence of a microorganism in a sample includes a housing that includes a base fixed with a first DNA primer having a nucleotide sequence that is complementary to a specific DNA sequence of the microorganism of interest, a fibrinogen-splitting agent that is bound with a second DNA primer having a nucleotide sequence that is also complementary to a DNA sequence of the microorganism of interest, a rinsing unit configured to rinse the housing, and a fibrinogen adding unit configured to add fibrinogen to the housing so that the fibrinogen chemically reacts with the fibrinogen-splitting agent to produce a viscous substance, an ultrasonic emitter configured to emit ultrasonic signal to the housing, and an ultrasonic receiver configured to receive ultrasonic signal from the housing and transmit the received ultrasonic signal to an ultrasonic analyzer, wherein the ultrasonic analyzer determines whether the microorganism of interest exists in the sample based on the received ultrasonic signal.

According to another aspect of the present invention, a method for detecting the presence of a microorganism in a sample, the method includes fixing a first DNA primer having a nucleotide sequence that is complementary to a DNA sequence of the microorganism of interest to abase in a housing, binding a fibrinogen-splitting agent with a second DNA primer having a nucleotide sequence that is complementary to a DNA sequence of the microorganism of interest, rinsing the housing by a buffer solution, adding fibrinogen to the housing so that the fibrinogen chemically reacts with the fibrinogen-splitting agent to produce a viscous substance, affects the transmission of ultrasonic signal from an ultrasonic emitter to an ultrasonic analyzer, wherein the algorithms within the ultrasonic analyzer determines whether the microorganism exists in the sample based on the received ultrasonic signal.

Figure 2:
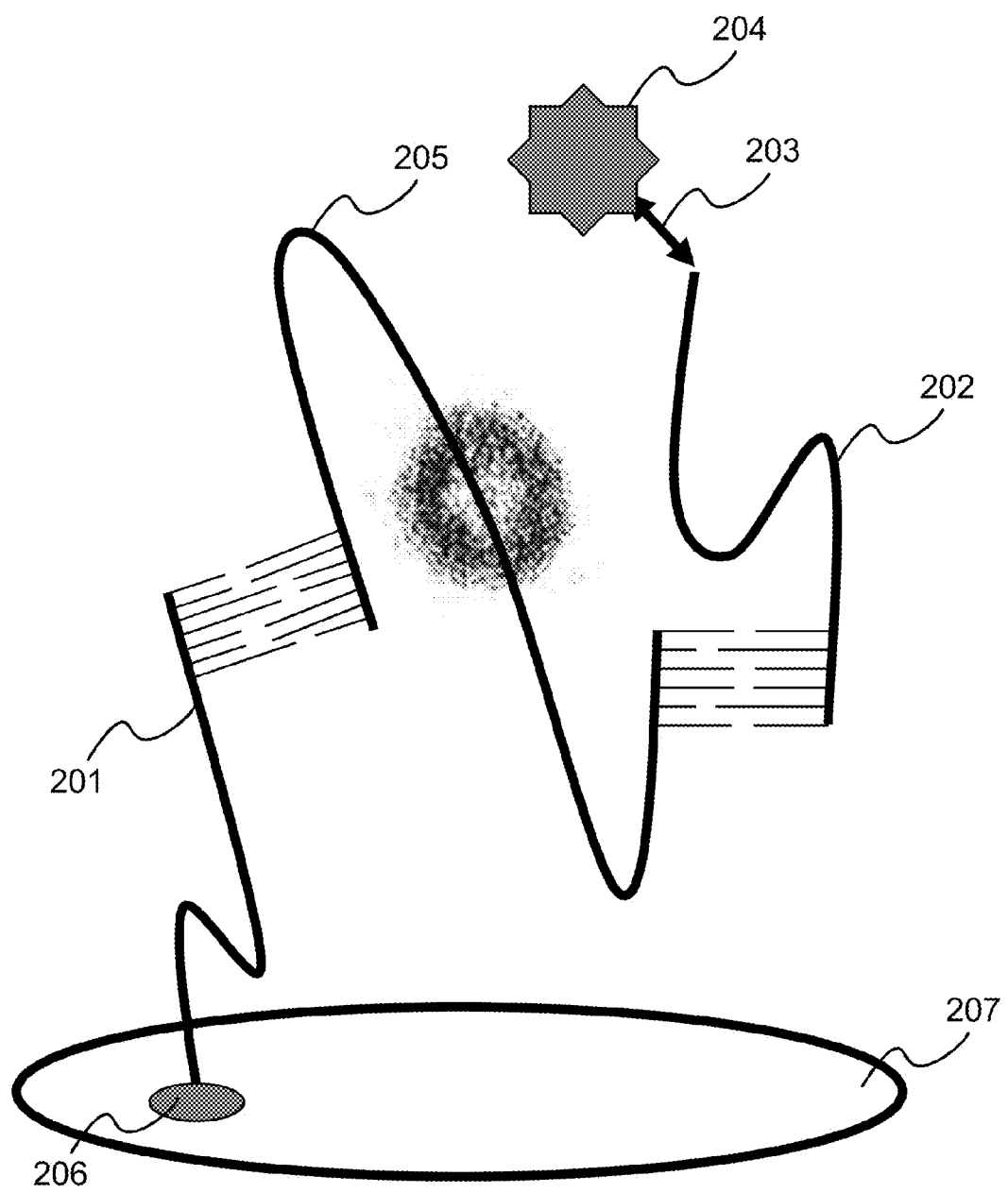
Figure 3A:
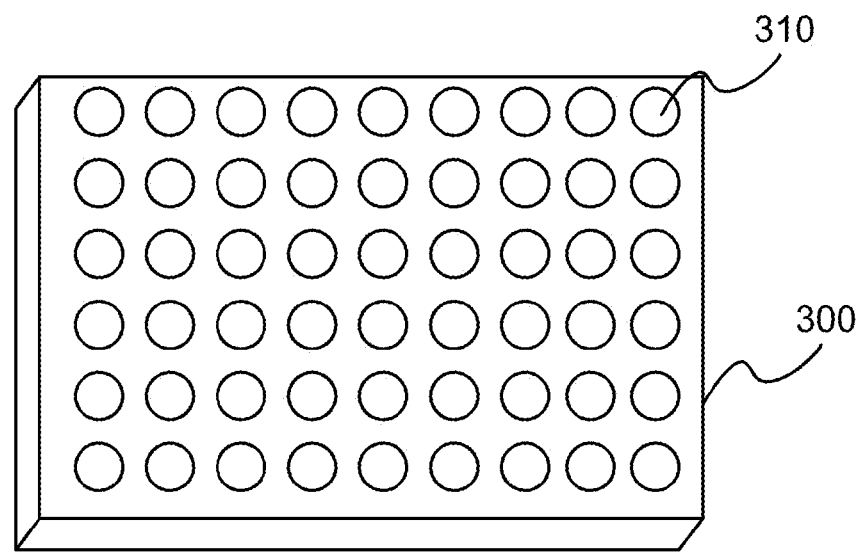
Figure 3B:
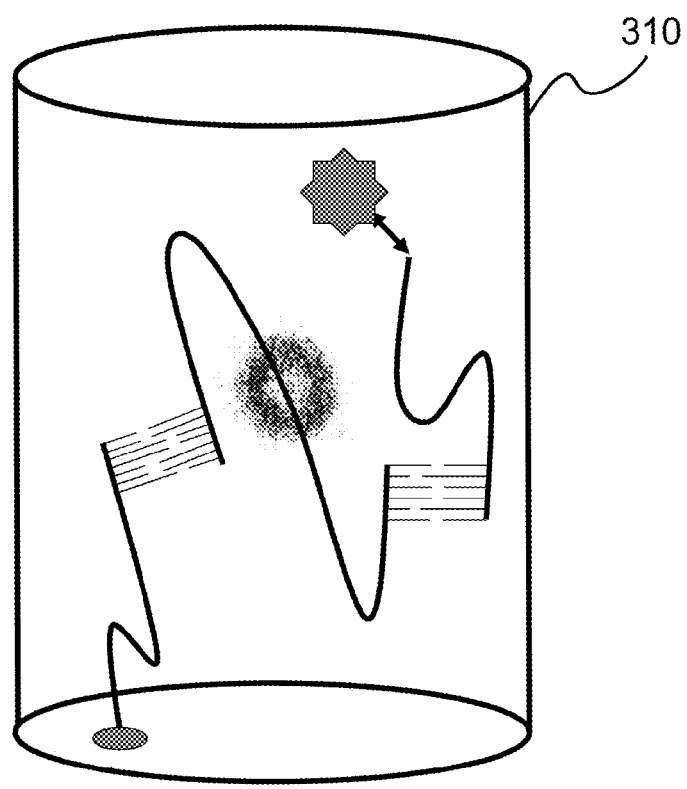

Further features and aspects of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is an exemplary configuration of an ultrasonic microorganism detection apparatus according to an embodiment of the present invention.

FIG. 2 is an example of anchoring of one side of a DNA primer to the housing (206) and the other side with complementary DNA sequence from a microorganism of interest from (201 to 205). Another stretch of complementary DNA on the microorganism of interest (205) binds to a second set of DNA primer (202) in which itself is linked to a fibrinogen-splitting agent (204) through a bifunctional chemical linker (203).

FIG. 3A is an example of a plastic (including polystyrene) microtiter plate with a plurality of wells in which the first set of primer DNA binds to the housing (206). Wells of the microtiter plate is not limited to circular shape.

FIG. 3B is an example of a well of a microtiter plate that contains a (first) strand of DNA primer with a stretch of complementary DNA from the microbes of interest while another stretch of this microbial DNA binds to a (second) strand of complementary DNA primer that is linked to a fibrinogen-splitting agent.

FIG. 4 is an example of a graph plotted using time against signals received in an ultrasonic receiver quantified either as voltage or amplitude received.

FIG. 5 illustrates an exemplary flow diagram according to an embodiment of the present invention.

DESCRIPTION OF THE EMBODIMENTS

Various embodiments of the present invention will be described below with reference to the accompanying drawings.

FIG. 1 illustrates an ultrasonic microorganism detection apparatus 100 according to an embodiment of the present invention. The detection apparatus includes a housing 110, an ultrasonic emitter 105, an ultrasonic receiver 106, a heating/cooling plate 103, one or more temperature sensors 108, reagent delivery and removal tubes 101 and 102, and a magnetic stirring mechanism 104.

Housing 110 is utilized for determining whether a microorganism is present in a sample therein. Housing 110 contains a polymer base, such as plastic (including polystyrene) (e.g. that used to manufacture an ELISA plate). Shape of the housing is not limited to rectangular, cylindrical or circular. The housing can be any enclosed structure that is suitable for containing fluid and allows the anchoring of a DNA primer. In addition, the housing 101 is suitable for the transmission of ultrasound there-through.

A "sample" refers to a substance to be tested for presence of a microorganism of interest. For instance, a sample may be substance (i.e., DNA from pathogen of interest) taken from a water reservoir, lake, a river, a body of water, sea, food surface, surface of any containers, biological fluids, tissue homogenates or an air sample. Suitable filters will be used to trap and concentrate microorganisms in the sample for further analysis by this invention. Microbial colonies obtained directly from suitable nutrient agar or cell culture plates where they grown could be used and can be added to the housing 110 directly. With heating to around 95° C. by the heating/cooling plate 103, DNA contents of the microbes will be released.

FIG. 2 is an example of bonding between a DNA primer and a target microorganism of interest in a sample. In this example, a plastic (e.g. polystyrene) polymer 207 is used to make up the base of the housing 110, and it is also bonded with a DNA primer 201. DNA primer 201 is chemically bonded (206) with base 207. The strand of DNA primer 201 may be fixed to the plastic (such as polystyrene) base by covalent attachment or non-covalent attachment depending upon reactivity between the plastic (e.g. polystyrene base) and the DNA primer. DNA primer 201 may be a nucleic acid strand such as chemically synthesized oligonucleotide, with a length of 6 to 30 bases long. It contains a specific nucleotide sequence that is complementary to part of the DNA sequence (205) of the target microorganism of interest. While only a single strand of DNA primer is illustrated, a plurality of strands of DNA primer may be fixed on the plastic base (e.g. polystyrene) in a similar manner.

The housing also includes fibrinogen-splitting agent 204 (e.g., α thrombin or active ingredients in various types of venoms including that of the Russell vipers or any other natural or synthetic fibrinogen-splitting chemicals or enzymes) that is bonded with a second DNA primer 202 via a bi-functional chemical linker 203. DNA primer 202 also contains a specific nucleotide sequence that is complementary to another part of the DNA sequence (205) of the target microorganism of interest in the sample. While only a single strand of DNA primer 202 is illustrated, a plurality of strands of DNA primer may be bonded with fibrinogen-splitting agent in a similar manner.

Plastic base 207 may be in a form of a microtiter plate well 300 as illustrated, for example, in FIG. 3A or in rectangular or any other shapes. The microtiter plate contains singularly or a plurality of wells 310. Each of the wells of a microtiter plate contains at least a single strand of DNA primer as illustrated in FIG. 3B. For illustrative purposes, the microorganism having a DNA sequence that is complementary to the DNA primer is shown FIG. 3B. Thus, the strand of DNA from the microorganism of interest in the sample is bonded with the two DNA primers.

The present invention also includes a stirring mechanism 104 such as stirring by a magnetic stirrer. The magnetic stirrer is capable of lightly mixing the mixture inside housing 110. As such, the movement enables the strands of DNA samples to hybridize and anneal with the strands of DNA primers.

Heating/cooling plate 103 is capable of heating or cooling the housing so that the mixture inside the housing operates at a range of desirable temperatures (e.g. 96° C. to ambient temperature) that is suitable for chemical reaction. Heating/cooling plate 103 may further include temperature sensors 108 for monitoring the temperature of the housing so that the housing operates at a desired temperature.

In the event that the DNA sample 205 is complementary to the DNA primer 201, the strand of DNA 205 of the microorganism (in the sample) will be hybridized (bound) to the DNA primer 201 as shown in FIG. 2. Also, the other part of the strand of DNA 205 will be hybridized (bound) with the DNA primer 202. That is, a complex consisting of the DNA primer 201 plus the complementary DNA from target microbes of interest (205) plus the other complementary DNA primer (202) plus bifunctional chemical linker (203) plus the fibrinogen-splitting agent (204) is formed. The whole complex is linked (206) to the plastic base (e.g. polystyrene) (207) covalently or non-covalently. However, in the event that the strand of DNA sample is not complementary to the DNA primer, hybridization will not take place and the complex will not be formed.

Thereafter, the mixture undergoes a water bath process that rinse off the excess microorganism that is not attached with the DNA primers. The water bath may contain an aqueous pH constant buffer solution which is entered through reagent tube opening 101. As stated previously, the strands of DNA which are not complementary to the DNA primers will not bond with the DNA primers. During this water bath process, unbounded DNA strands, fibrinogen-splitting agents and other loose substance are rinsed off and exit from housing through reagent tube opening 102. As such, only successfully hybridized DNA strands (i.e. in the form of the complex) will remain in the housing.

After the water bath process, purified fibrinogen solution or a mixture containing natural fibrinogen (e.g. plasma) or synthetic fibrinogen-like substance (e.g. chemical substrates) is added to housing 110 via regent tube opening 101. If fibrinogen-splitting agent still remains in housing 110 subsequent to the water bath process (because of linkage with the complex in which the target microbes is a part), the fibrinogen-splitting agent will chemically convert the natural or synthetic fibrinogen into a fibrin clot (or gel), which is a viscous type of mixture. In general, depending on the amount of sample size, the chemical reaction process takes a few minutes to complete.

Then, the ultrasonic emitter emits ultrasonic signal (or wave) through the housing 110. While the ultrasonic emitter/receiver may be activated any time before or after the addition of fibrinogen, the ultrasonic emitter/receiver must be activated prior to the mixture of the housing become viscous. The ultrasonic emitter contains one or more ultrasonic transducer (s) that produces ultrasonic signal. The emitted ultrasonic signal is received by the ultrasonic receiver at the other end of housing 110 as shown in FIG. 1. The received ultrasonic signal is transmitted to an ultrasonic analyzer (not shown) for analysis.

Figure 4:
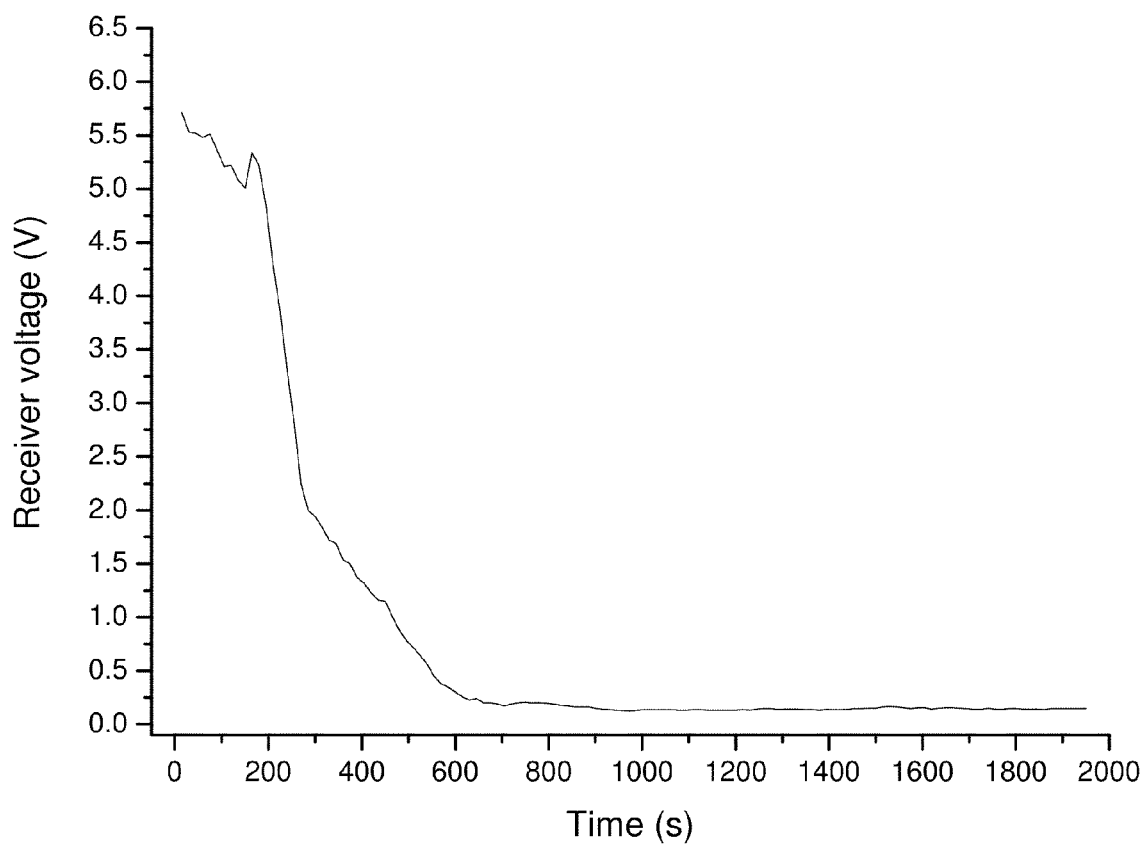

FIG. 4 shows a representative received ultrasonic signal which is displayed on an oscilloscope. As shown in the graph, the received ultrasonic signal in form of voltage decreases significantly to approximately 0.25 V after 10 minutes. Therefore, within a short period of time, we are able to determine that a change of viscosity of the complex exists. When ultrasonic signal passes through the clot, the ultrasonic signal amplitude would reduce significantly. Based on the change of viscosity, we can determine whether the target microorganism of interest exists in the mixture or not.

Attenuation in ultrasound measures the reduction in amplitude of the ultrasonic signal as a function of distance through a medium. Attenuation of the received ultrasonic signal can be calculated by the following equation:

$$\text{Attenuation} = 20(\log(V_{received})/(V_{transmitted}))/d (\text{dB/cm}) \quad (1)$$

where, $V_{received}$ is the received ultrasonic voltage, $V_{transmitted}$ is the transmitted ultrasonic voltage, and d is the distance between the ultrasonic emitter and receiver. Based on the value of attenuation, we can determine whether the content inside housing 110 has increased viscosity or not. When the value of attenuation decreases significantly, for example below 10 dB, we can determine that the content inside housing 110 has increased viscosity. The present invention does not limit the range of attenuation.

Figure 5:
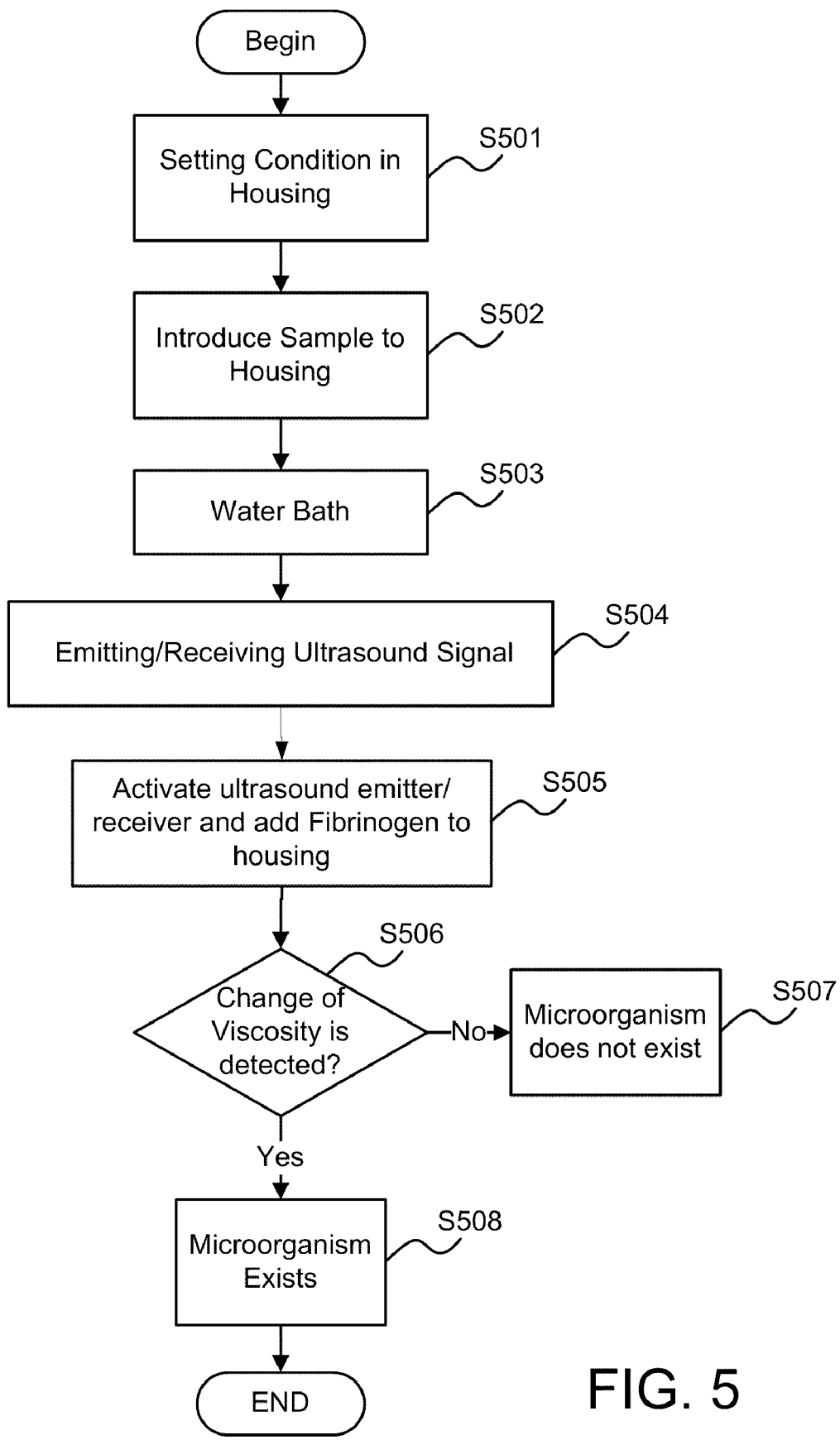

An exemplary process flow of detecting a DNA sequence from the target microbes of interest is illustrated in FIG. 5 in step S501, temperature condition of housing 110 is set. The housing 110 includes a plastic polymer base (including polystyrene) 207 that is bound with strands of DNA primers complementary to the DNA sequence of a specific type of microorganism. By activating the heating/cooling plate 103 (incubator), the housing 110 is adjusted to a suitable temperature (e.g. at around 90° C.). Thereafter, a sample is added to housing 110 in step S502. The sample may be added via an opening of the reagent tube 101. Then, the sample is mixed in the housing, for example, by stirring with a magnetic stirring mechanism 104. In general, the whole mixture is allowed to mix for 10 minutes. Subsequently, the housing 110 is cooled to about 56° C. or less before strands of DNA primers that are complementary to the DNA sequence (205) of a specific type of microorganism which were bonded with fibrinogen-splitting agent are added to housing 110. The whole mixture is allowed to mix for another 10 minutes.

Thereafter, the housing is rinsed with an aqueous pH constant buffer solution to rinse off any materials that are not hybridized with the DNA primers in step S503. After rinsing, the heating/cooling plate 103 (incubator) is activated again to bring the housing 110 to a suitable temperature for the fibrinogen-splitting enzyme to operate and to prevent fast degradation of the fibrinogen (e.g. at around 37° C.). Subsequently, fibrinogen solution is added to housing 110 (step S505). In addition, the ultrasonic emitter 105 is activated to emit ultrasonic signal through housing 110 (step S504). Please note that the ultrasonic emitter/receiver may be activated before or after the addition of fibrinogen.

The system allows the mixture to chemically react with the added fibrinogen (natural or synthetic fibrinogen-like substances) for a predetermined period of time. Then, an ultrasonic receiver receives the transmitted ultrasonic signal and transmits the received ultrasonic signal to an ultrasonic analyzer 109 for analysis. The ultrasonic analyzer may be built in the ultrasonic microorganism detection device or externally connected with the ultrasonic microorganism detection device via a wired or wireless connection.

Thereafter, the ultrasonic analyzer determines whether there is a viscosity change in housing 110 in step S506 based on received ultrasonic signal amplitude from the ultrasonic receiver. In the event that there is a viscosity change (YES in step S506), the ultrasonic analyzer determines that the microorganism exists in the sample (S508). On the other hand, if the viscosity of the complex does not change after a predetermined period of time (NO in step S507), the ultrasonic analyzer determines that the microorganism does not exist in the sample (S507). Then, the process ends.

The present invention may further include a display (e.g. an LCD display) that indicates whether a microorganism exists in the sample based on the received ultrasonic signal. For instance, in the event that there is a viscosity change, the ultrasonic analyzer 109 determines that the microorganism exists and the display will indicate that the microorganism exists. On the other hand, if the viscosity of the content inside housing 110 does not change after a predetermined period of time, the ultrasonic analyzer 109 determines that the microorganism does not exist and the display will indicate that the microorganism does not exist.

The operation of the ultrasonic analyzer 109 may be realized by a computer-executable program code that determines whether there is a viscosity change. The computer-executable program code may be stored in a computer-readable storage medium of the ultrasonic analyzer 109. For example, the present invention which could be very small in size which can be practiced in the forms of a system, an apparatus, a method, a program, a recording medium, etc.

By using the present detection method and apparatus, various microorganisms may be detected by using a corresponding set of DNA primers (equivalent to 201 and 203) having a DNA sequence complementary to the DNA sequence of the target microorganism of interest. In addition, users of the present ultrasonic microorganism detection apparatus do not require having extensive knowledge of biochemistry and molecular biology that is pre-requisite to perform florescence-based (e.g. PCR and RT-PCR) detection methods.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. An apparatus for detecting presence of a microorganism in a sample, comprising:
    a housing comprising:
        a base fixed with a first DNA primer having a nucleotide sequence that is complementary to a DNA sequence of the microorganism of interest;
        a fibrinogen-splitting agent that is bonded with a second DNA primer having a nucleotide sequence that is complementary to a DNA sequence of the microorganism;
        a rinsing unit configured to rinse the housing; and
        a fibrinogen adding unit configured to add fibrinogen to the housing so that the fibrinogen added will chemically reacts with the fibrinogen-splitting agent to produce a viscous substance;
    an ultrasonic emitter configured to emit ultrasonic signal to the housing; and
    an ultrasonic receiver configured to receive ultrasonic signal from the housing and transmit the received ultrasonic signal to an ultrasonic analyzer,
    wherein the ultrasonic analyzer determines whether the microorganism of interest exists in the sample based on the received ultrasonic signal.

2. The apparatus according to claim 1, wherein the base is a plastic, including polystyrene or other polymers.

3. The apparatus according to claim 2, wherein the base is a microtiter plate having one or more wells.

4. The apparatus according to claim 1, further comprises a heating/cooling plate and one or more temperature sensors that control temperature of the housing.

5. The apparatus according to claim 1, wherein the ultrasonic analyzer determines whether a viscosity change has occurred based on received ultrasonic signal amplitude from the ultrasonic receiver.

6. The apparatus according to claim 1, further comprises a magnetic stirring mechanism configured to mix substances inside the housing.

7. The apparatus according to claim 1, wherein the apparatus is portable and is capable of being used in field operations.

8. A method for detecting presence of a microorganism in a sample, the method comprising:
    fixing a first DNA primer having a nucleotide sequence that is complementary to a DNA sequence of the microorganism of interest to a base in a housing;
    bonding a fibrinogen-splitting agent with a second DNA primer having a nucleotide sequence that is complementary to a DNA sequence of the microorganism of interest;
    adding the sample which may contain the microorganisms of interest to form a mixture;
    incubating the mixture for a predetermined duration;
    rinsing the housing by a buffer solution;
    adding natural or synthetic fibrinogen to the housing so that the fibrinogen chemically reacts with the fibrinogen-splitting agent to produce a viscous substance;
    emitting ultrasonic signal to the housing;
    receiving the ultrasonic signal from the housing and transmitting the received ultrasonic signal to an ultrasonic analyzer,
    wherein the ultrasonic analyzer determines whether the microorganism exists in the sample based on the received ultrasonic signal.

9. The method according to claim 8, wherein the base is a plastic base that is made of polystyrene or other polymers.

10. The method according to claim 8, wherein the ultrasonic analyzer determines whether a viscosity change has occurred based on received ultrasonic signal amplitude from the received ultrasonic signal.

* * * * *